US008934607B2

(12) United States Patent
Ishibashi (10) Patent No.: US 8,934,607 B2
(45) Date of Patent: Jan. 13, 2015

(54) MEASURING APPARATUS AND MEASURING METHOD

(75) Inventor: Yasuhiko Ishibashi, Yokkaichi (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 286 days.

(21) Appl. No.: 13/601,232

(22) Filed: Aug. 31, 2012

(65) Prior Publication Data

US 2013/0243154 A1  Sep. 19, 2013

(30) Foreign Application Priority Data

Nov. 10, 2011 (JP) .................................. 2011-246559

(51) Int. Cl.
| | |
|---|---|
| G01N 23/20 | (2006.01) |
| G01B 15/04 | (2006.01) |
| G01N 21/956 | (2006.01) |
| H01L 21/66 | (2006.01) |

(52) U.S. Cl.
CPC ............... *B01N 23/20* (2013.01); *G01B 15/04* (2013.01); *H01L 22/12* (2013.01); *G01N 21/95607* (2013.01); *G01B 2210/56* (2013.01); *G01N 2021/95615* (2013.01)
USPC .................. 378/86; 378/54; 378/70; 378/82; 378/83; 378/90

(58) Field of Classification Search
CPC  G01N 23/20; G01N 23/2273; G01N 15/1475
USPC .............................. 378/70, 83, 86, 54, 84, 89
See application file for complete search history.

(56) References Cited

U.S. PATENT DOCUMENTS

| | | | | |
|---|---|---|---|---|
| 6,895,075 | B2 * | 5/2005 | Yokhin et al. .................... | 378/90 |
| 7,103,142 | B1 * | 9/2006 | Agnihotri et al. ................ | 378/82 |
| 7,248,669 | B2 * | 7/2007 | Ito et al. ........................... | 378/70 |

(Continued)

FOREIGN PATENT DOCUMENTS

| | | |
|---|---|---|
| JP | 2001-349849 | 12/2001 |
| JP | 2005-114475 | 4/2005 |

(Continued)

OTHER PUBLICATIONS

U.S. Appl. No. 14/021,127, filed Sep. 9, 2013, Ishibashi.

(Continued)

*Primary Examiner* — David A Vanore
(74) *Attorney, Agent, or Firm* — Oblon, Spivak, McClelland, Maier & Neustadt, L.L.P.

(57) ABSTRACT

In accordance with an embodiment, a measuring apparatus includes an electromagnetic wave applying unit, a detecting unit, a data processing unit, a film structure transforming unit, and a film structure measuring unit. The electromagnetic wave applying unit generates electromagnetic waves to apply it to a periodic structure of films on a substrate. The detecting unit detects the electromagnetic waves scattered or reflected by the substrate. The data processing unit calculates a surface shape of the periodic structure. The film structure transforming unit calculates a virtual film structure regarding the internal structure of the periodic structure. The film structure measuring unit calculates the thickness of each layer constituting the periodic structure by fitting a first reflectance profile by actual measurement regarding the periodic structure to a second reflectance profile obtained by a simulation using the virtual film structure to restructure the shape of the periodic structure.

16 Claims, 4 Drawing Sheets

(56) References Cited

U.S. PATENT DOCUMENTS

| | | | |
|---|---|---|---|
| 7,411,188 B2* | 8/2008 | deCecco et al. | 250/305 |
| 7,551,719 B2* | 6/2009 | Yokhin et al. | 378/90 |
| 7,692,131 B2* | 4/2010 | Fein et al. | 250/208.1 |
| 7,863,552 B2* | 1/2011 | Cartlidge et al. | 250/208.1 |
| 8,208,602 B2* | 6/2012 | Lee et al. | 378/119 |
| 8,269,167 B2* | 9/2012 | deCecco et al. | 250/305 |
| 8,610,059 B2* | 12/2013 | deCecco et al. | 250/305 |
| 2003/0157559 A1 | 8/2003 | Omote et al. | |
| 2006/0188062 A1* | 8/2006 | Agnihotri et al. | 378/82 |
| 2012/0051518 A1 | 3/2012 | Omote et al. | |
| 2012/0087473 A1* | 4/2012 | Omote et al. | 378/86 |
| 2012/0318974 A1* | 12/2012 | deCecco et al. | 250/305 |
| 2013/0243154 A1* | 9/2013 | Ishibashi | 378/54 |
| 2014/0070096 A1* | 3/2014 | deCecco et al. | 250/305 |

FOREIGN PATENT DOCUMENTS

| | | |
|---|---|---|
| JP | 2010-261737 | 11/2010 |
| JP | 2010-266381 | 11/2010 |

OTHER PUBLICATIONS

Hae-Jeong Lee et al., "Characterizing Nanoimprint Pattern Cross-Section and Fidelity from X-ray Reflectivity", Proc. of SPIE, vol. 6151, 61510N, 2006, pp. 61510N-1-61510N-7.

\* cited by examiner

MEASURING APPARATUS AND MEASURING METHOD

CROSS REFERENCE TO RELATED APPLICATIONS

This application is based upon and claims the benefit of priority from the prior Japanese Patent Application No. 2011-246559, filed on Nov. 10, 2011, the entire contents of which are incorporated herein by reference.

FIELD

Embodiments described herein relate generally to measuring apparatus and measuring method.

BACKGROUND

A semiconductor manufacturing process requires a technique to measure the width, height and wall angle of a pattern, and the micro shapes of the top and bottom of a wiring line. As a non-destructive and non-contact inspection apparatus, there has been known an apparatus which uses grazing incidence small angle X-ray scattering (GISAXS) that is reflective CD-SAXS. This apparatus uses the small angle scattering of X-rays to measure a shape, and totally reflects the X-rays on the surface of a substrate. This apparatus is therefore particularly advantageous to surface shape measurement. However, the apparatus has a drawback of being unable to measure an internal stack structure because the X-rays are totally reflected by the substrate surface and do not enter the structure. In the meantime, an X-ray reflectometer (XRR) technique is known as a technique to measure a stack structure. This technique uses interference resulting from the reflection of X-rays in each layer. This technique is generally used to measure an internal stack structure with no pattern structure. If there is a pattern structure, the measurement of the thickness of the internal structure is difficult because of interference conditions that are changed by the pattern structure and because of the effect of surface scattering.

DETAILED DESCRIPTION

In accordance with an embodiment, a measuring apparatus includes a stage, a stage control unit, an electromagnetic wave applying unit, an angle control unit, a detecting unit, a data processing unit, a film structure transforming unit, and a film structure measuring unit. The stage is configured to support a substrate on which a periodic structure comprising a plurality of films is formed. The stage control unit is configured to control the position and height of the stage. The electromagnetic wave applying unit is configured to generate electromagnetic waves and applies the electromagnetic waves to the substrate. The angle control unit is configured to control the elevation angle of the electromagnetic waves. The detecting unit is configured to detect the electromagnetic waves scattered or reflected by the substrate and measure the intensity of the electromagnetic waves scattered or reflected by the substrate. The data processing unit is configured to process a signal from the detecting unit to create a first scatter profile, fit the first scatter profile to a second scatter profile previously obtained by a simulation for the periodic structure, and thereby calculate a surface shape of the periodic structure. The film structure transforming unit is configured to calculate a virtual film structure regarding the surface structure of the periodic structure from the calculated surface shape, and calculate a virtual film structure regarding the internal structure of the periodic structure from reference data regarding the periodic structure. The film structure measuring unit is configured to set measurement conditions from the virtual film structure, control the stage control unit, the electromagnetic wave applying unit, the angle control unit, and the detecting unit in accordance with optical conditions and the measurement conditions, acquire a first reflectance profile by actual measurement regarding the periodic structure, calculate the thickness of each layer constituting the periodic structure by fitting the first reflectance profile to a second reflectance profile obtained by a simulation using the virtual film structure regarding the internal structure, and use the calculated thickness and the virtual film structure to restructure the shape of the periodic structure.

(A) Measuring Apparatus (1) Apparatus Configuration

Figure 1:
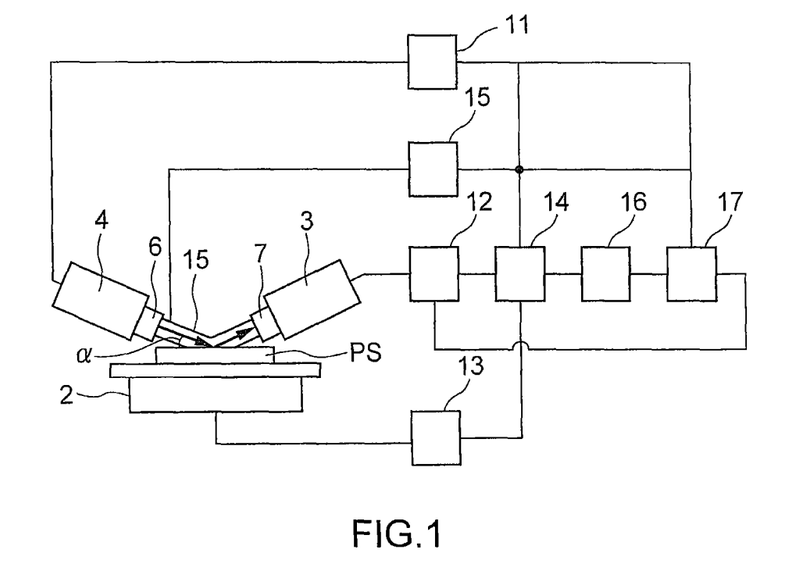
FIG. 1 is a block diagram showing a general configuration of a measuring apparatus according to an embodiment.

FIG. 1 is a block diagram showing a general configuration of a pattern measuring apparatus according to an embodiment. The measuring apparatus according to the present embodiment has both a function for measurement by grazing incidence small angle X-ray scattering (hereinafter referred to as "GISAXS measurement") and a function for measurement by X-ray reflectometer (hereinafter referred to as "XRR measurement").

More specifically, the measuring apparatus shown in FIG. 1 includes, as the main components, a stage 2, an X-ray tube 4, a light source controller 11, a goniometer 5, a monochromator 6, an attenuator 7, a two-dimensional detector 3, a data processor 12, a shape calculator 14, a goniometer controller 15, a stage controller 13, a film structure transformer 16, and a thickness calculator 17. The X-ray tube 4 is connected to the shape calculator 14 and the thickness calculator 17 via the light source controller 11. The two-dimensional detector 3 is connected to the shape calculator 14 and the thickness calculator 17 via the data processor 12. The shape calculator 14 is also connected to the stage controller 13 and the film structure transformer 16. The film structure transformer 16 is connected to the thickness calculator 17. The thickness calculator 17 is also connected to the goniometer controller 15 and the stage controller 13.

A wafer W is mounted on the upper surface of the stage 2, and the stage 2 supports the wafer W. Receiving a control signal from the stage controller 13, the stage 2 moves the wafer W in an X-Y-Z three-dimensional space in accordance with an unshown actuator, and also rotates the wafer W by an arbitrary rotation angle.

Figure 2:
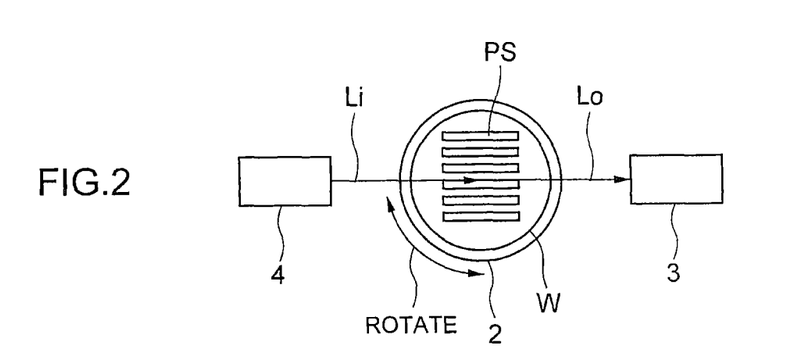
FIG. 2 is a plan view showing the relationship between an X-ray path and the direction of a pattern.

FIG. 2 is a plan view showing the relationship between an X-ray path and the direction of a pattern. As shown in FIG. 2, a periodic structure PS which is an inspection target is formed on the surface of the wafer W. The periodic structure includes not only a line-and-space structure shown in FIG. 2 but also a hole pattern structure arranged, for example, with a predetermined pitch in one direction or two directions perpendicular to each other, or a structure in which hole patterns and line patterns are mixed. In the present embodiment, the wafer W corresponds to, for example, a substrate. The substrate includes, but not limited to the wafer W, for example, a glass substrate, a compound semiconductor substrate, and a ceramic substrate.

The X-ray tube 4 includes a light source and a concave mirror (not shown). The light source is not particularly limited as long as the light source generates X-rays. In the case described in the present embodiment, for example, K$\alpha$-rays of Cu are used as a light source.

Receiving a control signal from the light source controller 11, the X-ray tube 4 generates X-rays Li having a wavelength of, for example, 1 nm or less. The optical path of the generated X-rays Li is adjusted by the concave mirror in the X-ray tube 4, and the X-rays Li are applied to the periodic structure PS at a desired elevation angle $\alpha$ (see FIG. 1). In the present embodiment, the X-ray tube 4 and the light source controller 11 correspond to, for example, an electromagnetic wave applying unit. However, the electromagnetic waves are not limited to the X-rays. When the periodic structure which is an inspection target has a large pitch of, for example, 1 µm or more, visible light of 300 nm to 700 nm may be used.

Receiving a control signal from the goniometer controller 15, the goniometer 5 adjusts the value of the elevation angle $\alpha$ of the X-rays Li together with the concave mirror. The elevation angle $\alpha$ selected for the GISAXS measurement is an angle of 1° or less at which the X-rays Li are totally reflected without penetrating the wafer W, and is preferably 0.2° or less. For the XRR measurement, the goniometer 5 changes the elevation angle $\alpha$ between 0 degrees and 10 degrees at every angular interval during the application of the X-rays Li so that the incidence angle is equal to the reflection angle. Accordingly, the X-rays enter perpendicularly to the line direction of the periodic structure PS from the point of the coherence length thereof.

The elevation angle $\alpha$ may be adjusted by providing a movable arm instead of or together with the goniometer 5. In the present embodiment, the goniometer 5 and the goniometer controller 15 correspond to, for example, an angle control unit.

The monochromator 6 only extracts a desired wavelength component from the X-rays Li generated by the X-ray tube 4. As a result, the X-rays Li are changed to a monochromatic parallel beam and applied to the wafer W.

The attenuator 7 damps, to desired intensity, X-rays Lo reflected by a pattern P to which the X-rays Li has been applied.

The two-dimensional detector 3 is located well apart from the periodic structure PS. The two-dimensional detector 3 detects, by light receiving elements, the X-rays Lo scattered by the periodic structure PS to which the X-rays Li has been applied, or the X-rays Lo which has been reflected by the periodic structure PS and adjusted to proper intensity by the attenuator 7. The two-dimensional detector 3 then measures the intensity of the X-rays Lo. The appearance of a light receiving unit of the two-dimensional detector 3 is shown in the perspective view of FIG. 3.

Figure 3:
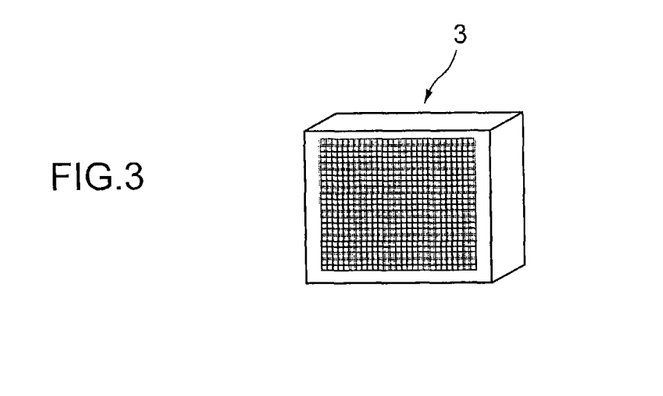
FIG. 3 is a perspective view showing the appearance of a light receiving unit of a two-dimensional detector.

The light receiving elements are two-dimensionally arranged in the light receiving unit of the two-dimensional detector 3. For the GISAXS measurement, each of the light receiving elements measures the intensity of the X-rays Lo diffracted by the periodic structure PS, and associates the measured intensity with its position, thereby creating a two-dimensional image of X-ray scatter intensity of the whole light receiving unit. During the measurement, the X-rays Li are applied while the stage 2 is being rotated between 0° and 10° (see FIG. 2). Therefore, the exposure by scattered X-rays continues, and the light receiving unit accumulates the continuously detected scatter intensity of the X-rays Lo.

For the XRR measurement, each of the light receiving elements of the two-dimensional detector 3 measures the intensity of the X-rays Lo which have entered and then been reflected by the periodic structure PS with the elevation angle $\alpha$ being changed by the goniometer 5 within a predetermined measurement angular range of, for example, 0 degrees to 10 degrees at every predetermined angular interval. Each of the light receiving elements associates the measured intensity with its position, thereby the light receiving unit creates a two-dimensional image of X-ray reflection intensity as a whole.

The data processor 12 adds up the scatter intensities measured by the light receiving elements of the two-dimensional detector 3. Thereby, the data processor 12 creates, for the GISAXS measurement, a two-dimensional X-ray scatter profile, and creates, for the XRR measurement, a reflectance profile including the added reflection intensities at the elevation angles $\alpha$ of 0 degrees to 10 degrees at the predetermined intervals adjusted by the goniometer 5.

In the GISAXS measurement, a taken scatter intensity image includes interference fringes which appear at an angle determined by Bragg's condition of diffraction in an azimuthal direction and an elevation angle direction. The data processor 12 divides the two-dimensional scatter intensity image in the azimuthal direction and the elevation angle direction, and calculates a scatter profile in each of the directions. Here, the profile in the azimuthal direction refers to a scatter profile in which the elevation angle of the incident X-rays Li is equal to the elevation angle of scattered X-rays Ls, and the profile in the elevation angle direction refers to the intensity change of diffraction peaks in the elevation angle direction.

Figure 4:
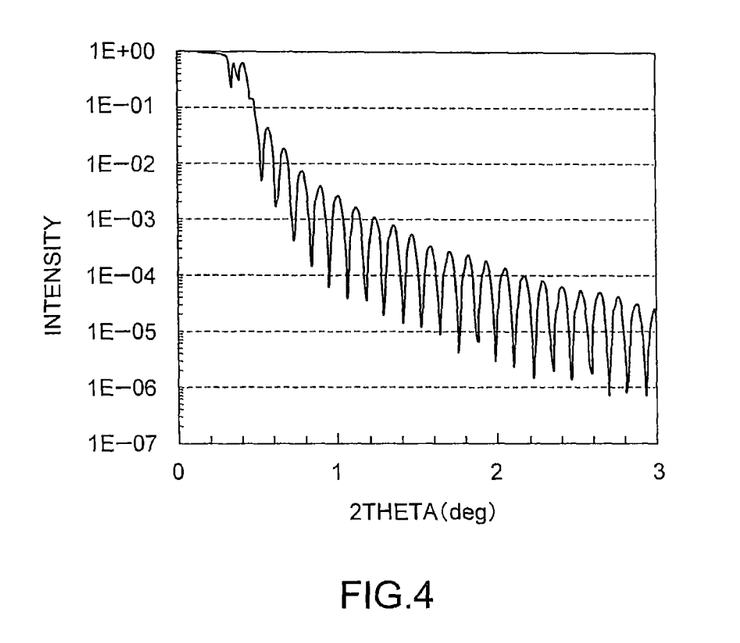
FIG. 4 is a graph showing an example of a reflectance profile obtained by the application of X-rays to a periodic structure that constitutes a stack layer.

If the X-rays Li having an azimuth nearly parallel to the longitudinal direction of the line pattern and having an elevation angle of 0.2° or less are applied to the line pattern, the X-rays Li are scattered due to the pattern. The scattered X-rays Ls cause interference, so that diffraction peaks appear in the scatter profile in the azimuthal direction, and an interference fringe appears in the elevation angle direction at each of the diffraction peaks. In the XRR measurement, when the periodic structure provided in the wafer W is a stack film, the X-rays are reflected by the surface of the wafer W and by the interface between films in the periodic structure and cause interference. If the intensity is plotted at every angular interval of the elevation angle $\alpha$, interference fringes varying in intensity with angle are observed, and a reflectance profile shown in FIG. 4 by way of example is obtained. The reflectance profile including the interference fringes can be acquired by calculation from optical conditions and stack information. The optical conditions in the XRR measurement include the wavelength and incidence angle (elevation angle direction) of the incident X-rays. The stack information includes thickness, interface roughness, electron density. If a path difference is calculated from the wavelength and incidence angle of the X-rays and the distance between interfaces in the stack film, a reflectance profile can be found by a simulation.

Receiving the scatter profile by actual measurement from the data processor 12, the shape calculator 14 checks the scatter profile against the profile obtained by a simulation (hereinafter referred to as a "simulation profile"), and performs fitting in a manner that the difference therebetween is minimized. The shape calculator 14 outputs, as a measurement value of the surface shape of the periodic structure PS, the value of a shape parameter providing the minimum fitting error, and supplies the value to the film structure transformer 16. In the present embodiment, the shape calculator 14 corresponds to, for example, a data processing unit, the scatter profile by actual measurement corresponds to, for example, a first scatter profile, and the simulation profile corresponds to, for example, the second scatter profile.

The simulation profile can be obtained by calculation from the optical conditions and pattern information. More specifically, for the periodic structure PS which is a measurement target, a section model is set from the pattern information including a sectional shape and a material and from the optical conditions, and the simulation profile is found from the section model by the volume integral of the sectional shape. A previously obtained simulation profile may be taken into the shape calculator 14, or the shape calculator 14 itself may create a simulation profile. In the present embodiment, the X-ray scatter profile thus created by a simulation corresponds to, for example, a second scatter profile.

The optical conditions refer to the wavelength and incidence angle (azimuthal direction, elevation angle direction) of the X-rays Li entering the wafer W, and so on. The pattern information includes the sectional shape and the electron density. The sectional shape means the shape of the edge portion of a surface pattern, and is a function represented by shape parameters including the pitch, CD, height, wall angle, top rounding, and bottom rounding.

Receiving the measurement value of the surface shape of the periodic structure PS from the shape calculator 14, the film structure transformer 16 calculates a virtual film structure regarding the surface structure of the periodic structure PS in accordance with a procedure described later in detail, and supplies the virtual film structure to the thickness calculator 17. Receiving reference data for the periodic structure PS from an unshown input unit, the film structure transformer 16 also calculates a stack model having electron density different from that of the surface structure regarding the internal structure of the periodic structure PS (hereinafter referred to as a "virtual film structure regarding the internal structure"), and supplies the virtual film structure to the thickness calculator 17. The reference data may be design data for the periodic structure PS, or may be data which is calculated from a section scanning electron microscope (SEM) or a transmission electron microscope (TEM) and which is obtained from the satisfactorily formed periodic structure PS.

The thickness calculator 17 determines conditions for the XRR measurement including a measurement angular range and a step angle from thickness information for the virtual film structure supplied from the film structure transformer 16, and sends the measurement conditions to the goniometer controller 15. The thickness calculator 17 also controls the light source controller 11 and the stage controller 13 in accordance with the optical conditions including the wavelength of the incident X-rays, and then performs the XRR measurement. The thickness calculator 17 receives, from the data processor 12, a reflectance profile by actual measurement regarding the pattern P (hereinafter referred to as an "actual measurement reflectance profile"). The thickness calculator 17 then analyses the obtained actual measurement reflectance profile, and thereby calculates the thickness of each layer in the internal structure of the pattern P. For the analysis, the thickness calculator 17 acquires a reflectance profile by a simulation for the virtual film structure regarding the internal structure supplied from the film structure transformer 16 (hereinafter referred to as a "simulation reflectance profile"). The thickness calculator 17 checks the actual measurement reflectance profile against the simulation reflectance profile, and performs fitting in a manner that the difference therebetween is minimized. The thickness calculator 17 then finds the thickness of each stack film and the value of the interface roughness that provide the minimum fitting error, and outputs the results as the thickness measurement value of the inside of a sectional structure. In the present embodiment, the actual measurement reflectance profile corresponds to, for example, a first reflectance profile, and the simulation reflectance profile corresponds to, for example, a second reflectance profile.

The thickness calculator 17 further restructures the overall shape of the periodic structure PS from the calculated thickness of each layer and from the thickness information for the virtual film structure supplied from the film structure transformer 16. In the present embodiment, the thickness calculator 17 corresponds to, for example, a film structure measuring unit.

The measuring apparatus according to the present embodiment includes the shape calculator 14 which measures the surface shape of the periodic structure in accordance with the GISAXS measurement, and the thickness calculator 17 which performs the XRR measurement based on the measurement result by the shape calculator 14 and analyses the obtained reflectance profile. It is therefore possible to measure both the surface structure and internal structure of the periodic structure with high accuracy.

(2) Measurement of Periodic Structure

Several methods of measuring the periodic structure PS by use of the measuring apparatus shown in FIG. 1 are described in detail with reference to FIG. 5 to FIG. 8. One characteristic of the methods described below includes sequentially performing both the GISAXS measurement and the XRR measurement, calculating the shape of a surface pattern from the GISAXS, performing the XRR measurement in accordance with the result of the calculation from the GISAXS, and restructuring the surface structure and internal structure of the periodic structure PS by the analysis of an obtained reflectance profile. The explanations are given below in order.

Figure 5:
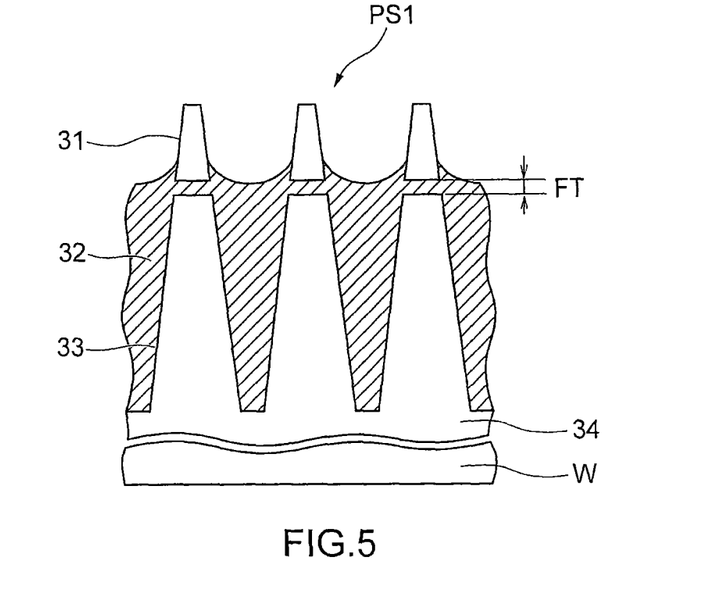
FIG. 5 is a sectional view showing an example of the periodic structure to which a measuring method according to an embodiment is applied.

FIG. 5 is a sectional view showing an example of a periodic structure to which the measuring method according to the present embodiment is applied.

A periodic structure PS1 shown in FIG. 5 includes a film 34 formed on the surface of the wafer W, a linear pattern 33 extending in the vertical direction of the drawing, a film 32, and a linear pattern 31 extending in the vertical direction of the drawing.

The pattern 33 is made of the same material as the film 34, and is provided on the film 34 with a predetermined period (pitch). The film 32 is formed to entirely cover the film 34 and the pattern 33 on the wafer W. The pattern 31 is formed on the film 32 in alignment with the top face of the pattern 33.

Here, assumption is made that the material of the pattern 31 is A, the material of the film 32 is B, and the material of the pattern 33 and the film 34 is C. A measurement target is assumed that the thickness FT of a region of the film 32 between the pattern 31 and the film 32.

First, the surface shape of the periodic structure is measured by the GISAXS measurement. More specifically, the shape calculator 14 generates various control signals, and sends the control signals to the light source controller 11, the data processor 12, the stage controller 13, and the goniometer controller 15. The X-rays Li enter at a desired elevation angle α from the X-ray tube 4 parallel to the line direction of the periodic structure PS. The shape calculator 14 receives an actual measurement scatter profile obtained in the data processor 12 via the two-dimensional detector 3. The shape calculator 14 analyses the actual measurement scatter profile, and thereby obtains the surface shape of the periodic structure PS.

As described above, in order to analyze the scatter profile, optimum shape parameters are found by checking against and fitting to the simulation profile. The found shape parameters include the curvature radiuses of the top and bottom of the pattern 31, and the wall angle.

The shape calculator 14 restructures the surface structure of the periodic structure PS from the obtained shape parameter information, and sends the resulting data to the film structure transformer 16.

Figure 6:
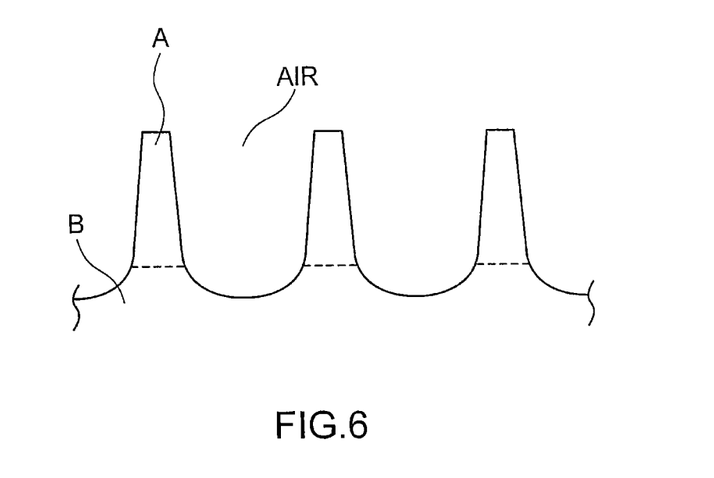
FIG. 6 is a diagram showing an example of a surface structure which is restructured from a measurement value of a surface shape obtained by GISAXS regarding the periodic structure shown in FIG. 5.

An example of a surface structure restructured from the measurement value of the surface shape obtained by the GISAXS measurement is shown in FIG. 6. As apparent from FIG. 6, a surface shape including the material A and the material B is obtained.

The film structure transformer 16 then regards the restructured surface structure of the periodic structure PS as a layer having a density gradient, and thus calculates a virtual film structure.

More specifically, the surface shape shown in FIG. 6 is divided into a plurality of regions in the height direction, and the materials A and B and an air volume ratio in each region are found. Effective electron density in each region is determined from the obtained volume ratio and the electron density of each of the materials A and B. The thickness and electron density of each of the layers that constitute the surface structure of the periodic structure PS are found to calculate the virtual film structure. The calculated virtual film structure is sent to the thickness calculator 17 from the film structure transformer 16.

Receiving reference data for the periodic structure PS from an unshown input unit, the film structure transformer 16 also calculates a virtual film structure for the internal structure having electron density different from that of the surface structure regarding the internal structure of the periodic structure PS, and supplies the calculated virtual film structure to the thickness calculator 17. The reference data may be design data for the periodic structure PS1, or may be data which is obtained from the section SEM or the TEM and which is obtained from the satisfactorily formed periodic structure PS1. In the calculation of the virtual structure regarding the internal structure, there may be a layer in which a plurality of materials are mixed, for example, there may be a layer in which the material B and the material C are mixed as shown in the periodic structure PS1 shown in FIG. 5. In this case, the ratio of the line width of the line pattern is found when the virtual film structure is calculated. Effective electron density of the mixture layer is calculated, and the result is used in the calculation of the virtual film structure regarding the internal structure.

The GISAXS measurement is followed by the XRR measurement. First, from thickness information for the virtual film structure supplied from the film structure transformer 16, the thickness calculator 17 sets the angular range and angular interval of the elevation angle α to be changed when the X-rays Li are applied to the wafer W in the XRR measurement. The thickness calculator 17 sends the angular range and angular interval to the goniometer controller 15 as measurement conditions.

The thickness calculator 17 then creates a reflectance profile by a simulation for the virtual film structure regarding the internal structure supplied from the film structure transformer 16.

Controlling the goniometer 5 via the goniometer controller 15 and moving the stage 2 via the stage controller 13, the thickness calculator 17 then applies the X-rays Li to the wafer W from the X-ray tube 4 via the light source controller 11 under the above-mentioned measurement conditions. The two-dimensional detector 3 measures the intensity of the reflected X-rays Lo from the wafer W, and the thickness calculator 17 receives the actual measurement reflectance profile created by the data processor 12.

The thickness calculator 17 then checks the actual measurement reflectance profile against the simulation reflectance profile, and performs fitting in a manner that the difference therebetween is minimized. The thickness calculator 17 finds the thickness of each stack film and the value of the interface roughness that provide the minimum fitting error, and outputs the results as the thickness measurement value of the inside of the periodic structure.

Finally, the thickness calculator 17 restructures the overall structure of the periodic structure PS1 including the surface structure and the internal structure. As a result, both the surface structure and the internal structure can be measured. The thickness FT (see FIG. 5) which is a measurement target can also be easily calculated from the restructured overall structure of the periodic structure PS1.

When the height of the surface pattern is small, for example, about 2 to 3 nm in the measurement target periodic structure, a more suitable virtual film structure can be calculated if the surface structure is regarded as a film greatly varying in height rather than as a layer having a density gradient as described above. The measurement of such a periodic structure is described as a modification of the present embodiment.

Figure 7:
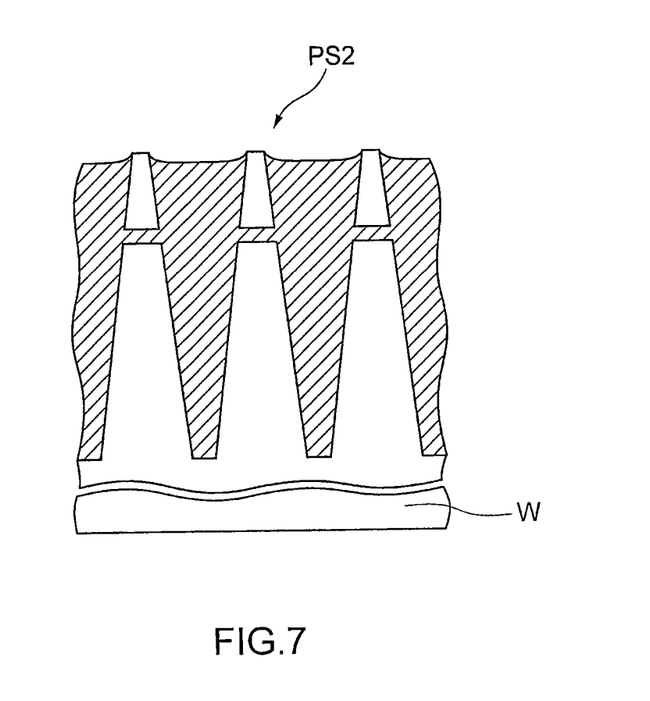
FIG. 7 is a sectional view showing an example of a periodic structure to which a measuring method according to a modification is applied.

An example of such a periodic structure having small surface pattern height is shown in a sectional view of FIG. 7. Such a periodic structure PS2 can also be measured by the measuring apparatus shown in FIG. 1.

First, the surface structure of the periodic structure PS2 is measured by the GISAXS measurement as in the measuring method described above. The shape calculator 14 finds various shape parameters such as the line width, the height, the wall angle, and the curvature radiuses of the top and bottom, and sends the shape parameters to the film structure transformer 16. The film structure transformer 16 finds the cross sectional area of the surface pattern structure from the supplied shape parameter information, and divides the cross sectional area by the pitch to calculate the virtual thickness of the surface pattern.

Surface roughness is found from the difference between the height of each point of the surface pattern structure and the thickness of the outermost surface structure. The thickness and roughness thus obtained are used to calculate a virtual film structure.

As in the measuring method described above, the XRR measurement is performed after the GISAXS measurement to measure the thickness of the inside of the periodic structure PS2 and restructure the overall structure of the periodic structure PS2.

Finally, necessary shape parameters such as thickness are calculated from the restructured overall structure of the periodic structure PS2.

As described above, according to the present modification, it is possible to measure both the surface structure and the internal structure with high accuracy even in the case of a surface structure having little variations.

(B) Measuring Method

Figure 8:
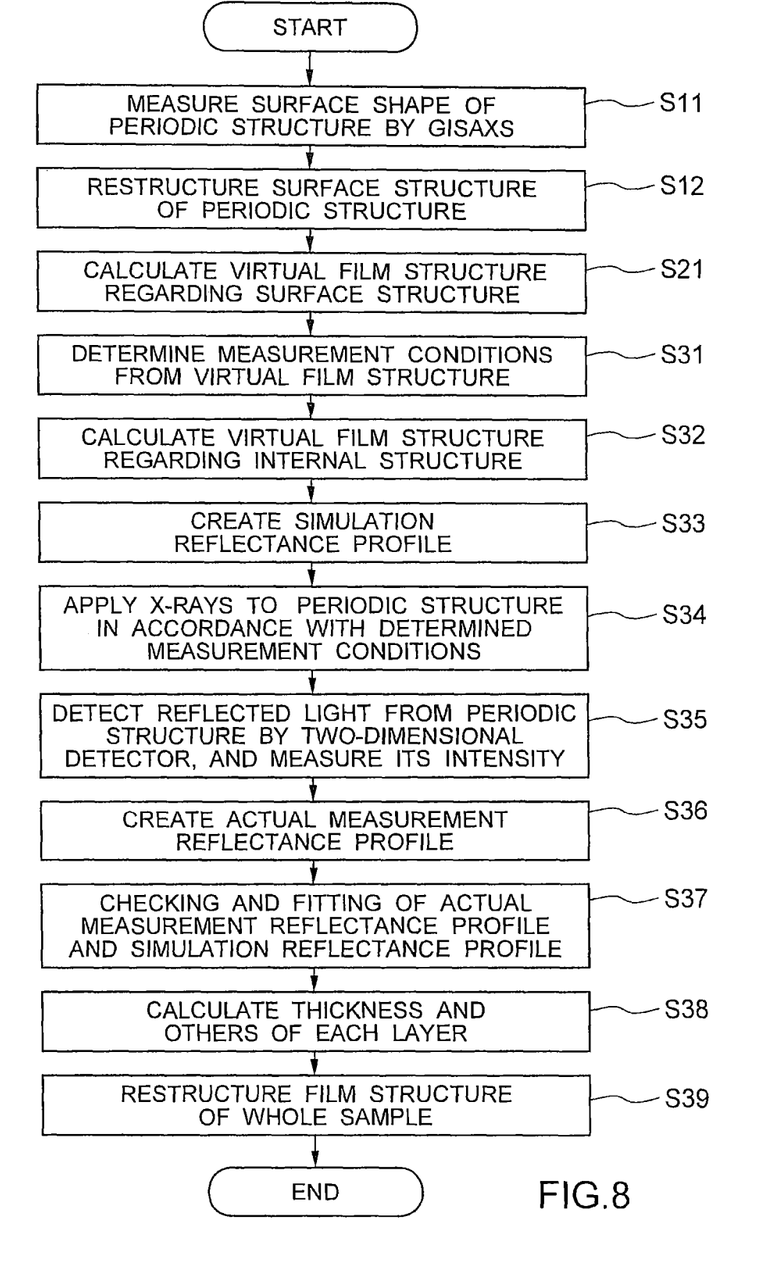
FIG. 8 is a flowchart showing a general procedure of the measuring method according to an embodiment.

The measuring method according to an embodiment is described with reference to the flowchart in FIG. 8.

First, the surface structure of a periodic structure which is a measurement target is measured by the GISAXS measurement (step S11).

The surface structure of the periodic structure is then restructured from the measurement result (step S12), and a virtual film structure is calculated accordingly (step S21). As described above, one way to calculate the virtual film structure is to regard the surface structure of the periodic structure as a layer having a density gradient and thus find the thickness and electron density of each of the layers that constitute the surface structure. Another way is to, when the height of the surface pattern is small, regard the surface structure as a film greatly varying in height and thus find its thickness and height variation.

Measurement conditions are then determined from the virtual film structure (step S31).

A virtual film structure regarding the internal structure of the periodic structure is then calculated by using design data for the periodic structure or reference data based on a measurement value from the section TEM (step S32), and a simulation reflectance profile is created (step S33).

X-rays are then applied to the periodic structure in accordance with the measurement conditions determined in step S31 (step S34). The reflected light from the periodic structure is detected by the two-dimensional detector to measure its intensity (step S35), and an actual measurement reflectance profile is created (step S36).

The obtained actual measurement reflectance profile is then checked against the simulation reflectance profile, and the thickness of each layer inside the periodic structure and the value of the interface roughness are calculated by fitting (step S38).

Finally, the film structure of the whole periodic structure is restructured from the virtual film structure obtained in step S21 and the measurement value of the internal structure obtained in step S38 (step S39).

Although the actual measurement reflectance profile is created after the creation of the simulation reflectance profile in the procedure described above, these profiles are not exclusively created in this order. The actual measurement reflectance profile may be first created, and then the simulation reflectance profile may be created and checked against and fitted to the actual measurement reflectance profile.

According to the measuring method of the present embodiment, the surface shape of the periodic structure is measured by the GISAXS measurement, and in accordance with the measurement result, the XRR measurement is performed, and then the obtained reflectance profile is analyzed. It is therefore possible to measure both the surface structure and the internal structure with high accuracy.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A measuring apparatus comprising:
   a stage configured to support a substrate on which a periodic structure comprising a plurality of films is formed;
   a stage control unit configured to control the position and height of the stage;
   an electromagnetic wave applying unit configured to generate electromagnetic waves and applies the electromagnetic waves to the substrate;
   an angle control unit configured to control an elevation angle of the electromagnetic waves;
   a detecting unit configured to detect the electromagnetic waves scattered or reflected by an substrate and measure an intensity of the electromagnetic waves scattered or reflected by the substrate;
   a data processing unit configured to process a signal from the detecting unit to create a first scatter profile, fit the first scatter profile to a second scatter profile previously obtained by a simulation for the periodic structure, and thereby calculate a surface shape of the periodic structure;
   a film structure transforming unit configured to calculate a virtual film structure regarding a surface structure of the periodic structure from the calculated surface shape, and calculate the virtual film structure regarding an internal structure of the periodic structure from reference data regarding the periodic structure; and
   a film structure measuring unit configured to set measurement conditions from the virtual film structure, control the stage control unit, the electromagnetic wave applying unit, the angle control unit, and the detecting unit in accordance with optical conditions and the measurement conditions, acquire a first reflectance profile by actual measurement regarding the periodic structure, calculate a thickness of each layer constituting the periodic structure by fitting the first reflectance profile to a second reflectance profile obtained by a simulation using the virtual film structure regarding the internal structure, and use the calculated thickness and the virtual film structure to restructure the shape of the periodic structure.

2. The apparatus of claim 1,
   wherein the film structure transforming unit divides the surface structure into a plurality of regions in a height direction in accordance with material data for each material constituting the surface structure of the periodic structure and in accordance with the surface shape of the periodic structure calculated by the data processing unit, calculates, for each of the divided regions, effective electron density in each layer of the surface structure from a material volume ratio and the electron density of each material, and finds the thicknesses and electron densities of a plurality of layers with density gradients, and calculates the virtual film structure regarding the internal structure based on the obtained thickness and electron densities.

3. The apparatus of claim 1,
   wherein the film structure transforming unit divides a cross sectional area of the surface structure of the periodic structure by a period of the periodic structure to find a virtual thickness of the surface structure, and finds a height variation of the surface structure from a difference between a value of the obtained thickness and each point of the surface structure to calculate the virtual film structure regarding the surface structure.

4. The apparatus of claim 1,
wherein the film structure transforming unit regards the surface structure of the periodic structure as a layer having a density gradient, and then finds the thickness and electron density of each layer constituting the surface structure to calculate the virtual film structure.

5. The apparatus of claim 1,
wherein the film structure transforming unit regards the surface structure as a film with a large variation in height, and thus find its thickness and height variation when a height of a pattern on the surface of the periodic structure is approximately 2 nm to approximately 3 nm.

6. The apparatus of claim 1,
wherein the film structure measuring unit controls the angle control unit so that the elevation angle changes at every predetermined angular interval.

7. The apparatus of claim 1,
wherein the electromagnetic wave applying unit generates X-rays of 1 nm or less in wavelength as the electromagnetic waves.

8. The apparatus of claim 1,
wherein the electromagnetic wave applying unit generates visible light of 300 nm to 700 nm as the electromagnetic waves when a pitch of the periodic structure is 1 µm or more.

9. A measuring method comprising:
applying electromagnetic waves to a substrate on which a periodic structure comprising a plurality of films is formed, and processing a signal obtained by measuring an intensity of the scattered electromagnetic waves to calculate a surface shape of the periodic structure;
calculating the virtual film structure regarding a surface structure of the periodic structure from the calculated surface shape;
calculating the virtual film structure regarding an internal structure of the periodic structure from reference data regarding the periodic structure;
setting measurement conditions from the virtual film structure;
applying electromagnetic waves to the substrate in accordance with the set measurement conditions and optical conditions, and processing a signal obtained by detecting the intensity of the scattered electromagnetic waves to acquire a first reflectance profile by actual measurement regarding the periodic structure;
calculating a thickness of each layer constituting an inside of the periodic structure by fitting the first reflectance profile to a second reflectance profile obtained by a simulation using the virtual film structure regarding the internal structure; and
using the calculated thickness and the virtual film structure to restructure the shape of the periodic structure.

10. The method of claim 9,
wherein calculating the virtual film structure regarding the internal structure comprises:
dividing the surface structure into a plurality of regions in a height direction in accordance with the calculated surface shape of the periodic structure and in accordance with material data for each material constituting the surface structure of the periodic structure,
calculating, for each of the divided regions, effective electron density in each layer of the surface structure from a material volume ratio and the electron density of each material, and
finding the thicknesses and electron densities of a plurality of layers having density gradients.

11. The method of claim 9,
wherein calculating the virtual film structure regarding the surface structure comprises:
dividing a cross sectional area of the surface structure of the periodic structure by a period of the periodic structure to find a virtual thickness of the surface structure, and
finding a height variation of the surface structure from a difference between a value of the obtained thickness and each point of the surface structure.

12. The method of claim 9,
wherein the virtual film structure is calculated by regarding the surface structure of the periodic structure as a layer having a density gradient and then finding the thickness and electron density of each layer constituting the surface structure.

13. The method of claim 9,
wherein a height of a pattern on the surface of the periodic structure is approximately 2 nm to approximately 3 nm, and
the virtual film structure is calculated by regarding the surface structure as a film with a large variation in height and thus finding its thickness and height variation.

14. The method of claim 9,
wherein the electromagnetic waves are applied so that an elevation angle thereof changes at every predetermined angular interval.

15. The method of claim 9,
wherein the electromagnetic waves are X-rays of 1 nm or less in wavelength.

16. The method of claim 9,
wherein the electromagnetic waves are visible light of 300 nm to 700 nm when a pitch of the periodic structure is 1 µm or more.

* * * * *